US008594478B2

(12) United States Patent
Seftel et al.

(10) Patent No.: US 8,594,478 B2
(45) Date of Patent: Nov. 26, 2013

(54) METHOD AND APPARATUS FOR STORING A LASER OPTICAL FIBER

(75) Inventors: Allen D. Seftel, Cherry Hill, NJ (US); Stephen T. Pastor, Sagamore Hills, OH (US); Richard Alan Williams, Akron, OH (US)

(73) Assignee: Patient Pocket, LLC, Cherry Hill, NJ (US)

( * ) Notice: Subject to any disclaimer, the term of this patent is extended or adjusted under 35 U.S.C. 154(b) by 106 days.

(21) Appl. No.: 13/063,881

(22) PCT Filed: Mar. 22, 2010

(86) PCT No.: PCT/US2010/028141
§ 371 (c)(1),
(2), (4) Date: Mar. 14, 2011

(87) PCT Pub. No.: WO2010/108175
PCT Pub. Date: Sep. 23, 2010

(65) Prior Publication Data
US 2012/0002933 A1    Jan. 5, 2012

Related U.S. Application Data

(60) Provisional application No. 61/161,840, filed on Mar. 20, 2009.

(51) Int. Cl.
*G02B 6/00* (2006.01)
(52) U.S. Cl.
USPC .......................................... 385/135; 385/139
(58) Field of Classification Search
None
See application file for complete search history.

(56) References Cited

U.S. PATENT DOCUMENTS

| 4,316,204 | A | * | 2/1982 | Inagaki et al. | 257/432 |
|---|---|---|---|---|---|
| 4,558,093 | A | * | 12/1985 | Hatzenbuhler et al. | 524/837 |
| 4,760,845 | A | * | 8/1988 | Kovalcheck | 606/28 |
| 4,952,012 | A | | 8/1990 | Stamnitz | |
| 4,998,795 | A | * | 3/1991 | Bowen et al. | 385/78 |
| 5,219,650 | A | | 6/1993 | Ritter | |
| 5,263,585 | A | | 11/1993 | Lawhon et al. | |
| 5,809,198 | A | * | 9/1998 | Weber et al. | 385/139 |
| 5,873,865 | A | | 2/1999 | Horzewski et al. | |
| 5,930,440 | A | * | 7/1999 | Bar-Or | 385/136 |
| 6,144,791 | A | | 11/2000 | Wach et al. | |
| 6,643,447 | B2 | * | 11/2003 | Guy et al. | 385/139 |
| 6,840,238 | B1 | | 1/2005 | Van Hegelsom | |
| 6,966,791 | B1 | * | 11/2005 | Farr | 439/367 |
| 7,485,116 | B2 | * | 2/2009 | Cao | 606/10 |

(Continued)

*Primary Examiner* — Mike Stahl
(74) *Attorney, Agent, or Firm* — Howard M. Cohn

(57) ABSTRACT

A laser optical fiber storage system (10) and method for temporarily storing a proximal section (12) of an elongated flexible optical fiber (14). The system and method include a storage housing (16) having a closed end (18) and an open end (20). A plug stopper (22) being laser energy impermeable is disposed within the open end of the elongated storage housing to prevent the escape of laser light from within the storage housing. The plug stopper has an access port (24) adapted to enable the proximal section of the optical fiber to be loaded into and withdrawn from the housing. The storage housing is configured to temporarily retain the proximal section of the elongated flexible optical fiber in an elongated configuration or in a spiral configuration. Structure (29) within the storage housing prevents laser light from passing through walls of the storage housing.

20 Claims, 8 Drawing Sheets

(56) References Cited

U.S. PATENT DOCUMENTS

| | | |
|---|---|---|
| 8,047,663 B2 * | 11/2011 | Pang et al. .................... 359/614 |
| 2004/0170369 A1 * | 9/2004 | Pons ............................. 385/135 |
| 2005/0203496 A1 * | 9/2005 | Ritchie et al. .................. 606/15 |
| 2007/0270788 A1 * | 11/2007 | Nahen et al. .................... 606/15 |
| 2007/0292098 A1 * | 12/2007 | Kokkinos ...................... 385/139 |
| 2009/0060444 A1 * | 3/2009 | Muendel ....................... 385/137 |
| 2011/0085775 A1 * | 4/2011 | Van Zuylen et al. .......... 385/135 |
| 2013/0129297 A1 * | 5/2013 | Seftel et al. ................... 385/135 |

* cited by examiner

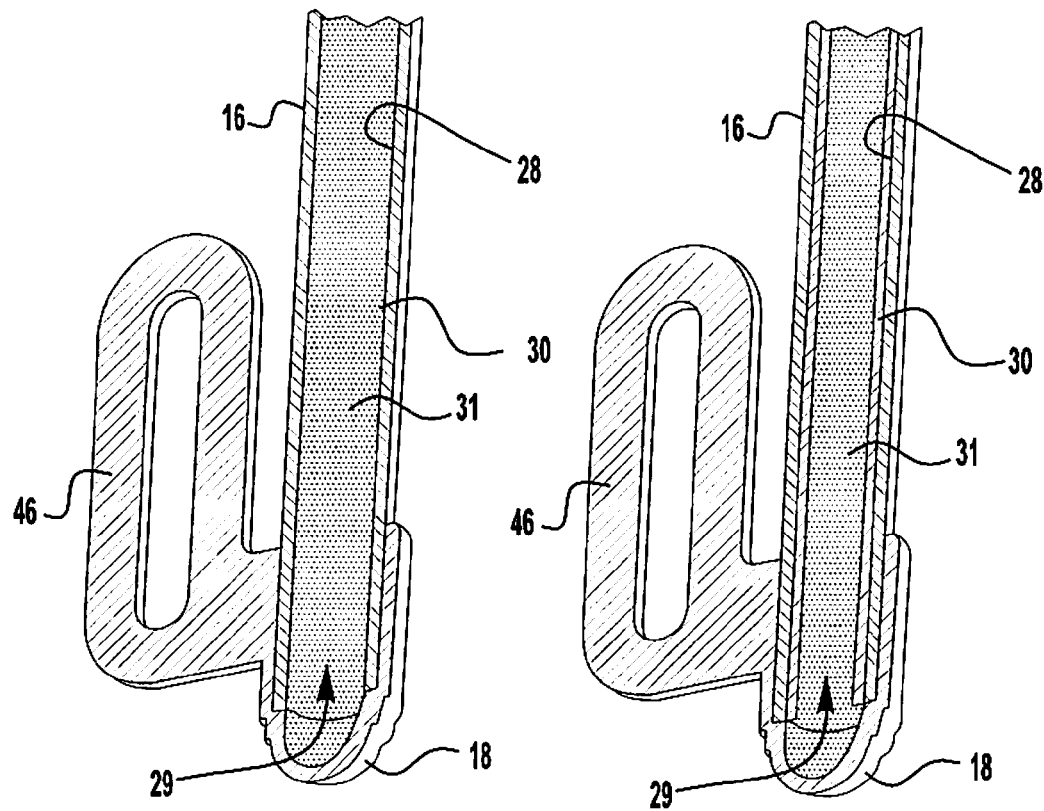
FIG. 3    FIG. 4
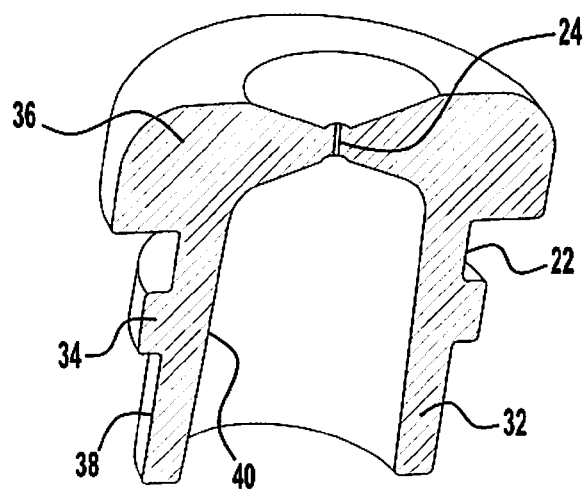
FIG. 5

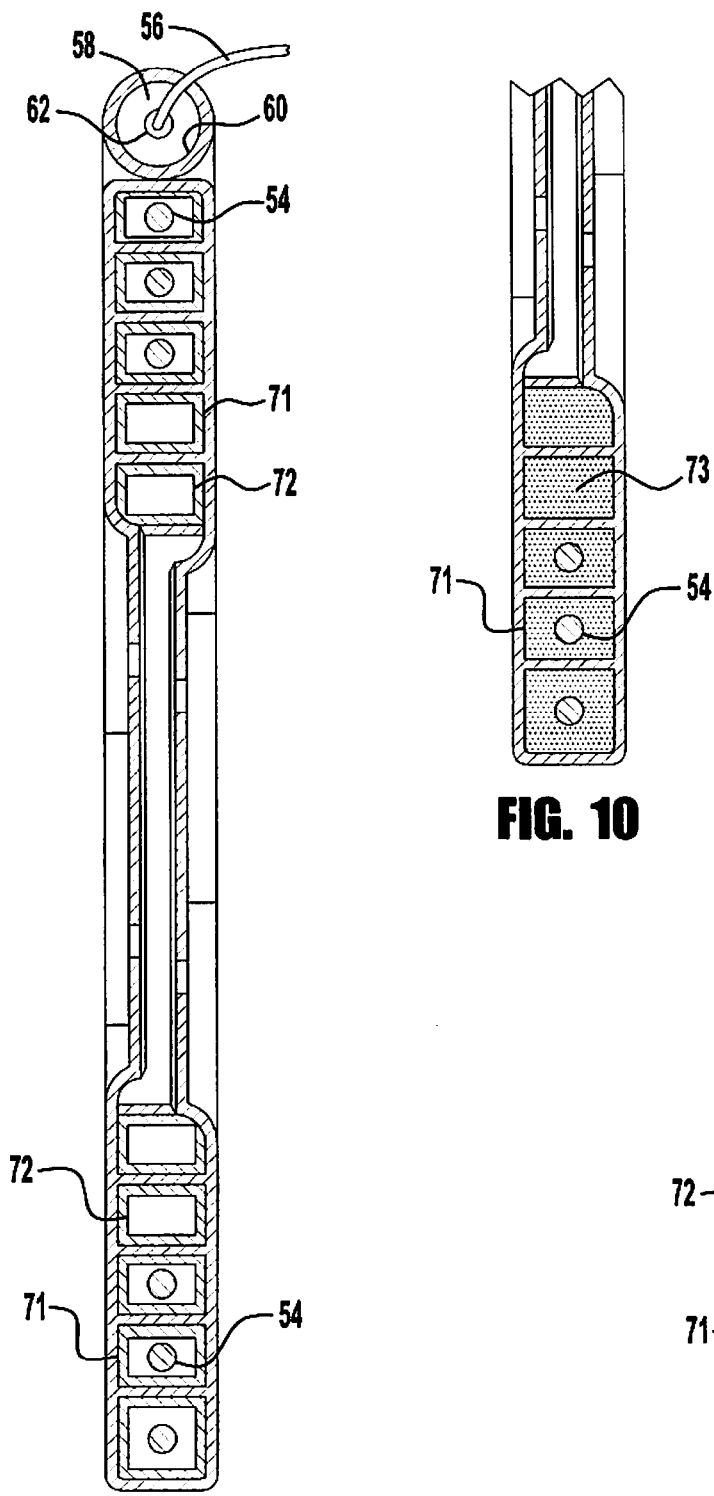

METHOD AND APPARATUS FOR STORING A LASER OPTICAL FIBER

CROSS-REFERENCE TO RELATED APPLICATIONS

This application claims the benefit of U.S. Provisional Patent Application No. 61/161,840 entitled "Housing For Fiber Optic Of Laser Delivery System And Housing for Non-Laser Delivery System" filed on Mar. 20, 2010, which is hereby expressly incorporated herein by reference.

TECHNICAL FIELD OF THE INVENTION

The invention relates to a method and apparatus for storing a laser optical fiber and more particularly to a method and apparatus for storing a laser optical fiber whereby laser light generated by the accidental discharge of the laser will not escape the laser optical fiber storage apparatus.

BACKGROUND OF THE INVENTION

Surgical laser devices or systems supply energy from a laser source, through such energy delivery systems as optical fiber delivery systems or waveguides like articulated arms, to the tissue of a patient. In a number of cases, a probe is connected to the distal end of the energy delivery system to facilitate the delivery of concentrated therapeutic energy to the tissue being treated.

Storage devices to house and dispense surgical catheters are well known in the art. These devices generally provide a protective covering for fragile and expensive surgical catheters. Some such devices highlight a storage function; others are specialized to dispense the encased catheter during an operation; still others are designed to perform both functions. Moreover, such devices can be designed to house a variety of different catheter types.

However, the devices known in the art suffer from a multitude of shortcomings.

Whereas surgical catheters come in a variety of lengths, many housing devices can only accommodate catheters of specific lengths. This specificity prevents such devices from being used with longer or shorter catheter lengths.

Another problem suffered by many catheter storage devices is that, when the catheter is removed from the housing, the catheter becomes tangled or kinked. This can make it difficult to handle the catheter with the precision required for surgical operations. Moreover, damage to the catheter can result from severe kinking.

Because the housing device will inevitably come into contact with the catheter itself, it is imperative that the housing be kept aseptic. Prior art housing devices, however often contain the catheters in narrow, hard-to-reach compartments. This construction makes it difficult to access storage areas and perform sterilization procedures.

While such housing apparatuses have been introduced for virtually every variety of surgical catheter, few if any have been designed for the storage and dispensing of optical laser fibers.

Laser devices or systems that have been designed for use in contact with tissue generally include a fiber optical cable affixed to a laser energy delivery system. Such devices offer a number of advantages over free-beam energy delivery systems: they significantly reduce the waste arising from the backscatter of laser energy from the tissue; they define a clear and precise area of irradiation; they protect the optical fiber or other energy delivery system from fouling; and they provide tactile feedback to the surgeon. Perhaps most importantly, the probe may be treated to absorb or scatter laser energy, or both, such that both radiated photonic energy and conducted thermal energy can be delivered to the tissue.

Optical laser fibers however are fragile and break easily. Housing units that are not constructed of light-tight material allow laser light to escape in the event of breakage, inadvertent firing and unreliable transmission.

Accordingly, housing systems designed for other types of surgical catheters are not generally suitable for use with optic fibers.

Surgical laser devices or systems supply energy from a laser source, through such energy delivery systems as fiber optical delivery systems or waveguides like articulated arms, to the tissue of a patient. In a number of cases, a probe is connected to the distal end of the energy delivery system to facilitate the delivery of concentrated therapeutic energy to the tissue being treated. From a general perspective, surgical laser devices or systems may be divided into two categories: those that are designed for use in contact with tissue, and those that are designed for use without contact with tissue.

The fiber optic components of the laser delivery systems are both expensive and fragile. It is not an uncommon problem during surgery that the laser fiber may break or become contaminated, resulting in an undue expense and frustration. The current invention seeks to rectify the aforementioned potential problems, and allow the user to protect the optical laser fiber, during the course of a medical procedure.

ASPECTS OF THE INVENTION

An aspect of the present invention includes providing an improved method and apparatus for suitable, cost effective temporary storage and dispensing of surgical optical fibers.

Another further aspect of the present invention is to provide a device that is able to resist burn-through by a medical laser beam for at least a desirable time interval.

A further aspect of the present invention is to provide a safety mechanism to protect the patient and the hospital staff from inadvertent firing of the optical laser fiber.

A still further aspect of the present invention is to protect a non-laser delivery system, such as a ureteroscope, during a procedure or surgery.

A yet further aspect of the present invention is to provide a device that maintains the sterility of a laser fiber optical during a procedure.

Another aspect of the present invention is to provide a cost effective system that reduces the chance for needing additional fibers during use or during a procedure.

SUMMARY OF THE INVENTION

This invention provides an improved apparatus and process for temporarily storing a section of an elongated flexible or rigid optical fiber.

According to the present invention, a laser optical fiber storage system for temporarily storing a proximal section of an elongated flexible optical fiber comprises an elongated storage housing having a closed end and an open end. A laser energy impermeable plug stopper is disposed within the open end of the elongated storage housing to prevent the escape of laser light from within the storage housing. The plug stopper has an access port adapted to enable the proximal section of the optical fiber to be loaded into and withdrawn from the housing. The storage housing is configured to temporarily retain the proximal section of the elongated flexible optical fiber in an elongated configuration. A structure within the storage housing prevents laser light from passing through walls of the storage housing.

Further according to the present invention, the structure within the storage housing for preventing laser light from passing through walls of the storage receptacle is an inner liner of silicone rubber which blocks laser beams.

Still further according to the present invention, the inner liner of silicone rubber is a flexible matrix containing material particles of a non-toxic material which is non-burnable when exposed to a medical laser beams.

Yet further according to the present invention, the inner liner is a coating of the materials that are substantially non-burnable when exposed to medical laser beams so as to resist penetration of the structure by the medical laser beams for at least a desirable time interval on the inner wall of the tubular housing.

Still further according to the present invention, the inner liner is configured as a tube which is sized to firmly fit against the inner wall of the tubular housing.

Moreover, according to the present invention, the structure within the storage housing for preventing laser light from passing through walls of the storage receptacle is a gel.

Also according to the present invention, the structure within the storage housing for preventing laser light from passing through walls of the storage housing is an inner liner of silicone rubber which blocks laser beams and a gel within the inner liner, together for preventing laser light from passing through walls of the storage receptacle.

Further according to the present invention, the access port extending through the plug stopper is generally contracted into a closed condition and expanded when the optical fiber is being pushed though and into the housing and then contracted to hold the optical fiber within the housing.

Still further according to the present invention, the storage housing includes at least one ring through which a strap is inserted for attaching the storage housing to a patient's body.

According to another embodiment of the present invention, a laser optical fiber storage system for temporarily storing a proximal section of an elongated flexible optical fiber, includes a storage housing configured to retain the proximal section of the optical fiber in a coiled configuration and to enable the complete removal of the proximal portion there from. A plug stopper is disposed within the open end of the storage housing to prevent the escape of laser light therefrom. The plug stopper has an access port through which the proximal portion of the optical fiber is loaded into and withdrawn from the storage housing. The storage housing is configured to temporarily retain the proximal section of the elongated flexible optical fiber in a coiled configuration. A structure within the storage receptacle prevents laser light from passing through walls of the storage housing.

Further, according to the another embodiment of present invention, the storage housing has a spiral shaped, closed channel to receive the proximal section of an elongated flexible optical fiber and configure the elongated flexible optical fiber in a coiled configuration.

Still further according to the another embodiment of present invention, the structure within the storage housing for preventing laser light from passing through walls of the storage receptacle is an inner liner of silicone rubber within the spiral shaped, closed channel which blocks laser beams.

Yet further according to the another embodiment of present invention, the inner liner is a coating of the materials that are substantially non-burnable when exposed to a medical laser beam so as to resist penetration of the structure by a medical laser beam for at least a desirable time interval through the storage housing.

Moreover according to the another embodiment of present invention, the inner liner is configured as a tube which is sized to fit within the spiral shaped closed channel of the storage housing.

And still further according to the another embodiment of present invention, the structure within the storage housing for preventing laser light from passing through walls of the storage housing is a gel which is within the spiral shaped closed channel of the storage housing.

And yet further according to the another embodiment of present invention, the structure within the storage housing for preventing laser light from passing through walls of the storage housing is an inner liner of silicone rubber which blocks laser beams and a gel within the inner liner for preventing laser light from passing through walls of the storage receptacle.

Further according to the another embodiment of present invention, the access port through the plug stopper is generally contracted into a closed condition and can expand for the optical fiber be pushed though and into the housing and then contract to hold the optical fiber within the housing place.

According to the another embodiment of present invention, a method of is disclosed for temporarily storing a proximal section of an elongated flexible optical fiber. The elongated storage housing is provided with an open end. A laser energy impermeable, plug stopper is disposed within the open end of the elongated storage housing to prevent the escape of laser light from within the storage housing. The proximal portion of the optical fiber is loaded into the housing through an access port through the plug stopper. The proximal section of the elongated flexible optical fiber is temporarily retained within the storage housing.

Further according to the another embodiment of present invention, a method is disclosed for temporarily storing a proximal section of an elongated flexible optical fiber including the step of retaining the proximal section of the elongated flexible optical fiber in an elongated configuration.

Also according to the another embodiment of present invention, a method of is disclosed for temporarily storing a proximal section including the step of retaining the proximal section of the elongated flexible optical fiber being loaded in a spiral configuration.

DESCRIPTION OF THE DRAWINGS

The structure, operation, and advantages of the present invention will become further apparent upon consideration of the following description taken in conjunction with the accompanying figures (FIGs.). The figures are intended to be illustrative, not limiting. Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

If shading or cross-hatching is used, it is intended to be of use in distinguishing one element from another (such as a cross-hatched element from a neighboring un-shaded element. It should be understood that it is not intended to limit the disclosure due to shading or cross-hatching in the drawing figures.

In the drawings accompanying the description that follows, both reference numerals and legends (labels, text descriptions) may be used to identify elements. If legends are pro

FIG. 3 shows cross sectional view of the device for storing a laser optical fiber taken through line 2-2 of FIG. 1, but including an optical fiber and incorporating a gel according to the present invention.

FIG. 4 shows cross sectional view of the device for storing a laser optical fiber taken through line 2-2 of FIG. 1, but including an optical fiber and incorporating a gel within an inner liner, according to the present invention.

FIG. 5 shows the plug stopper for closing both devices for storing a laser optical fiber shown in FIGS. 1 and 7, attached to the leg of a person, according to the present invention.

FIG. 9 shows cross sectional view of the device for storing a laser optical fiber taken through line 9-9 of FIG. 7 but including an optical fiber as shown in FIG. 8, according to the present invention.

FIG. 10 shows cross sectional view of the device for storing a laser optical fiber taken through line 9-9 of FIG. 7, incorporating a gel and an optical fiber, according to the present invention.

FIG. 11 shows cross sectional view of the device for storing a laser optical fiber taken through line 9-9 of FIG. 7, incorporating a gel within an inner liner and an optical fiber, according to the present invention.

DESCRIPTION OF THE PREFERRED EMBODIMENTS

In the description that follows, numerous details are set forth in order to provide a thorough understanding of the present invention. It will be appreciated by those skilled in the art that variations of these specific details are possible while still achieving the results of the present invention. Well-known processing steps and materials are generally not described in detail in order to avoid unnecessarily obfuscating the description of the present invention.

In the description that follows, exemplary dimensions may be presented for an illustrative embodiment of the invention. The dimensions should not be interpreted as limiting. They are included to provide a sense of proportion. Generally speaking, it is the relationship between various elements, where they are located, their contrasting compositions, and sometimes their relative sizes that is of significance.

Figure 1:
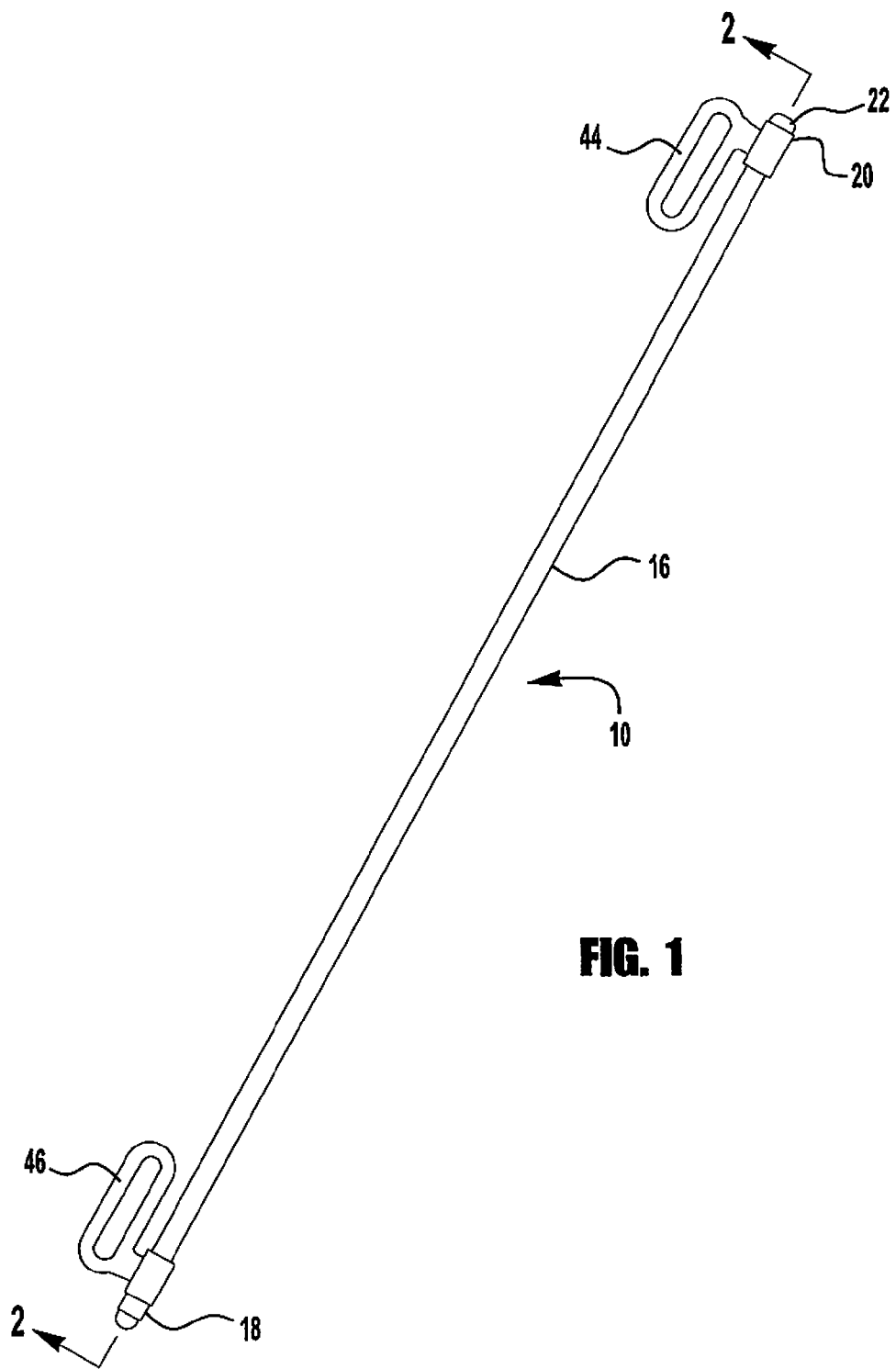
- FIG. 1 shows a three dimensional view of a device for storing a laser optical fiber, according to the present invention.
Figure 2:
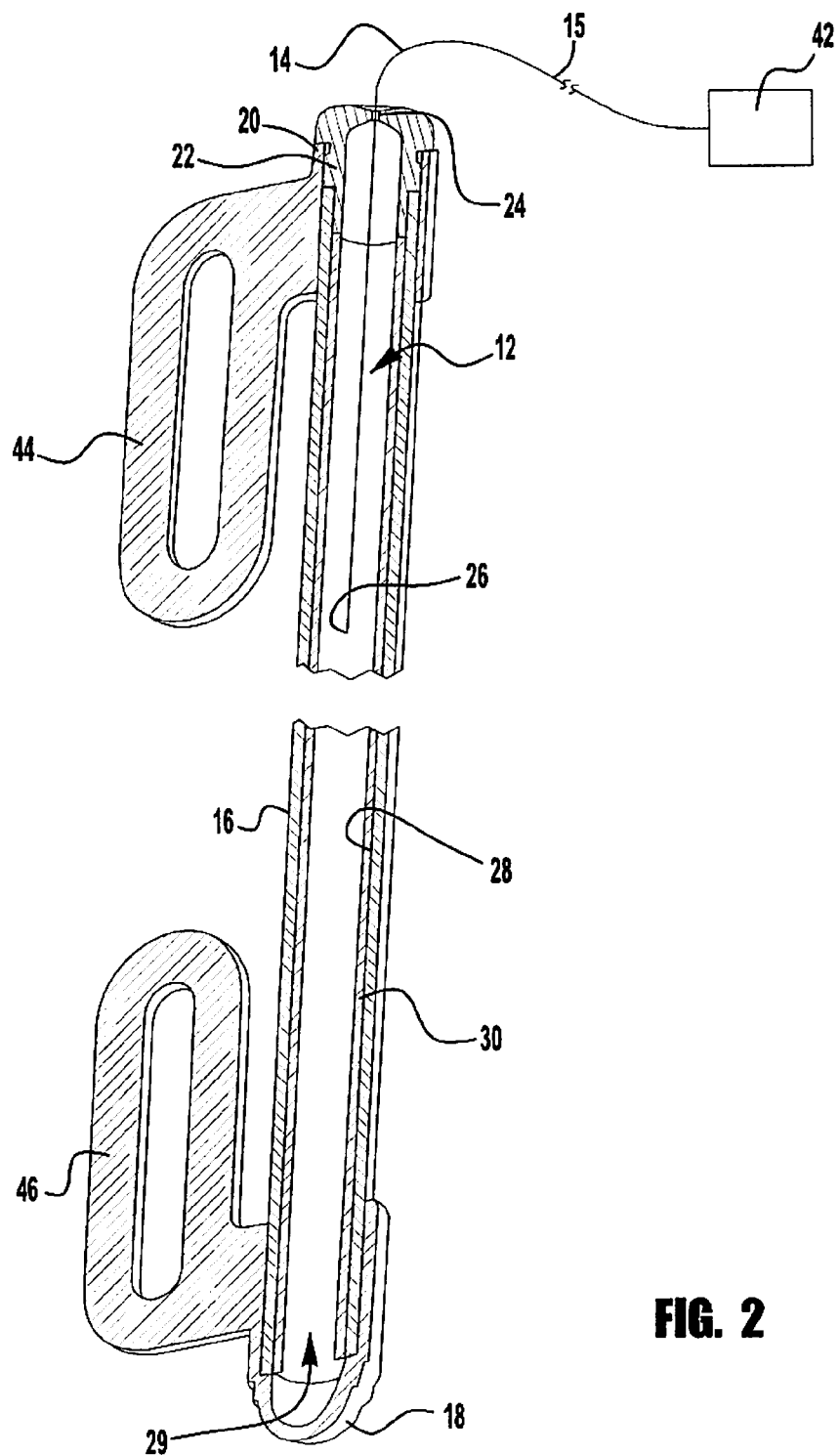
FIG. 2 shows cross sectional view of the device for storing a laser optical fiber taken through line 2-2 of FIG. 1, but including an optical fiber, according to the present invention.

Referring to FIG. 1, there is shown a three dimensional view of a laser optical fiber storage system 10 for temporarily storing the proximal section 12 of an elongated flexible optical fiber 14 (See FIG. 2). The laser optical fiber storage system 10 includes an elongated storage receptacle or housing 16 having a closed end 18 and an open end 20.

A plug stopper 22 (see FIG. 5) is disposed within the open end 20 of the elongated storage housing 16 to prevent the escape of laser light from within the storage housing, as discussed in detail hereinafter. The plug stopper 22 has an access port 24 that is adapted to enable the proximal section 12 of the optical fiber 14 to be loaded into and withdrawn from the storage housing 16.

As shown in FIG. 2, the storage housing 16 is configured to temporarily retain the proximal section 12 of the elongated flexible optical fiber 14 in an elongated configuration. It is preferable that the proximal end 26 of the optical fiber 14 does not contact the inner wall 28 of the receptacle 16. However, it is within the terms of the invention that the proximal end 26 can contact the inner wall of the receptacle when the inner wall is constructed of a variety of materials as discussed hereinafter. The optical fiber 14 is formed from a material having sufficient torsional rigidity so that the proximal section 12 can be inserted into the storage housing by movement of applied force to the proximal end 26 of the optical fiber transmitting controllably by the distal section 15 of the optical fiber.

The storage receptacle 16 is preferably constructed as a tubular housing with a rounded structurally closed end 18 and an open end 20. The tubular housing 16 can be constructed of a variety of materials, such as but not limited to, for example, plastic, polymers and aluminum. The housing 16 is hollow and may be of any suitable shape to carry out the aims of the present invention. As shown, housing 16 has a hollow, cylindrically shaped section having an opening 20 at one end and a closed end section 18, such as for example as a cupped shaped section, at the opposite end. It is understood that both the cylindrically shaped section 16 and the cupped shaped section 20 can be of any desired shape. The opening 20 receives a closure element 22, such as for example, a medical grade rubber stopper 22 having an access port 24 there through. The medical grade stopper material is designed to be laser energy impermeable, as with the rest of housing 10.

Preferably, the hollow housing 16 has a structure 29, such as an inner liner 30 of a material such as silicone rubber (no latex) which blocks laser beams of all wavelengths. The silicone rubber can be loaded with a substantial amount of particulate material. For example, as described in U.S. Pat. No. 5,219,650, which is incorporated in its entirety herein, the silicone rubber can be constructed as a flexible, relatively thin structure containing a substantial amount of generally uniformly distributed material particles captured within a flexible matrix. The particles can be formed of a non-toxic material which is non-burnable when exposed to a medical laser beam and undergoes a phase change from a solid state at a sufficiently high temperature so as to resist penetration of the structure by a medical laser beam for at least a desirable time interval and wherein the material particles have a size in the range from about 300 mesh to about 30 mesh to enhance the ability of the structure to resist burn-through by a medical laser beam.

Another material that is substantially non-burnable when exposed to a medical laser beam so as to resist penetration of the structure by a medical laser beam for at least a desirable time interval is a silicone rubber (no latex) which blocks laser beams of all wavelengths from Lasermet Ltd. of Georgia.

The inner liner 30 can be a coating of the materials that are substantially non-burnable when exposed to a medical laser beam so as to resist penetration of the structure by a medical laser beam for at least a desirable time interval, as previously mentioned, on the inner wall 28 of the tubular housing 16.

Alternatively, the inner liner 30 can be constructed as a tube which is sized to firmly fit against the inner wall 28 of the tubular housing 16. This type of silicone rubber is substantially non-burnable when exposed to a medical laser beam and is able to resist burn-through by the medical laser beam of the inner liner and the housing wall when exposed to a medical laser beam for at least a desirable time interval.

As shown in FIG. 3, it is also within the terms to fill the tubular housing 16 with a gel 31, such as for example, an acoustic gel with the trade name LithoClear from Sonotech Corporation of Washington. The gel, which is approximately 90% water, provides very good protection to the tubular housing 16 and is able to resist burn-through of the housing wall when exposed to a medical laser beam for a period of time. The gel will be contained within the tubular housing 16 by the plug stopper 22. Note that the gel is very viscous and as such can easily be contained within the tubular housing 16 by the stopper 22.

Another embodiment of the present invention is the incorporation of the inner liner 30 in combination with the gel, described directly above, and illustrated in FIG. 4.

Referring again to plug stopper 22, it can be constructed of a flexible material, such as rubber. The plug stopper includes a cylindrical sidewall 32, with or without a collar 34, encircling the outer wall 38 of the sidewall. The collar 34 serves to create a tight fit between the plug stopper 22 and the inner wall 28 of tubular housing 16. The plug stopper 22 includes head portion 36 that is larger than the diameter of the tubular housing and in particular the inner cylindrical sidewall 28 of the tubular housing 16 and enables a user to insert and remove the plug stopper from the inner sidewall. An access port 24 through which an optical fiber 24 can be inserted into the tubular housing extends through the head portion 36 of plug stopper 22. Note that the access port 24 is generally contracted into a closed condition. However, port 24 can expand to allow the optical fiber 14 to be pushed though and into the housing 16. Once the optical fiber 14 is in the access port 24, it contracts and holds the optical fiber in place so that it won't slip out of the housing 16. The closed access port 24 also keeps the gel within housing 16 when it is incorporated into the design. Moreover, when the optical fiber 14 is removed from the gel filled housing 16, the gripping of the fiber by the contracted access port 24 causes the gel to be wiped off of the fiber as it is being withdrawn. Another advantage of the closed access port 24 is that when an optical fiber 14 is inserted through the access port and into the housing, the closure of port 24 grips the optical fiber prevents any stray laser light from escaping the tubular housing 16 in the case that the laser is accidentally fired off.

Figure 6:
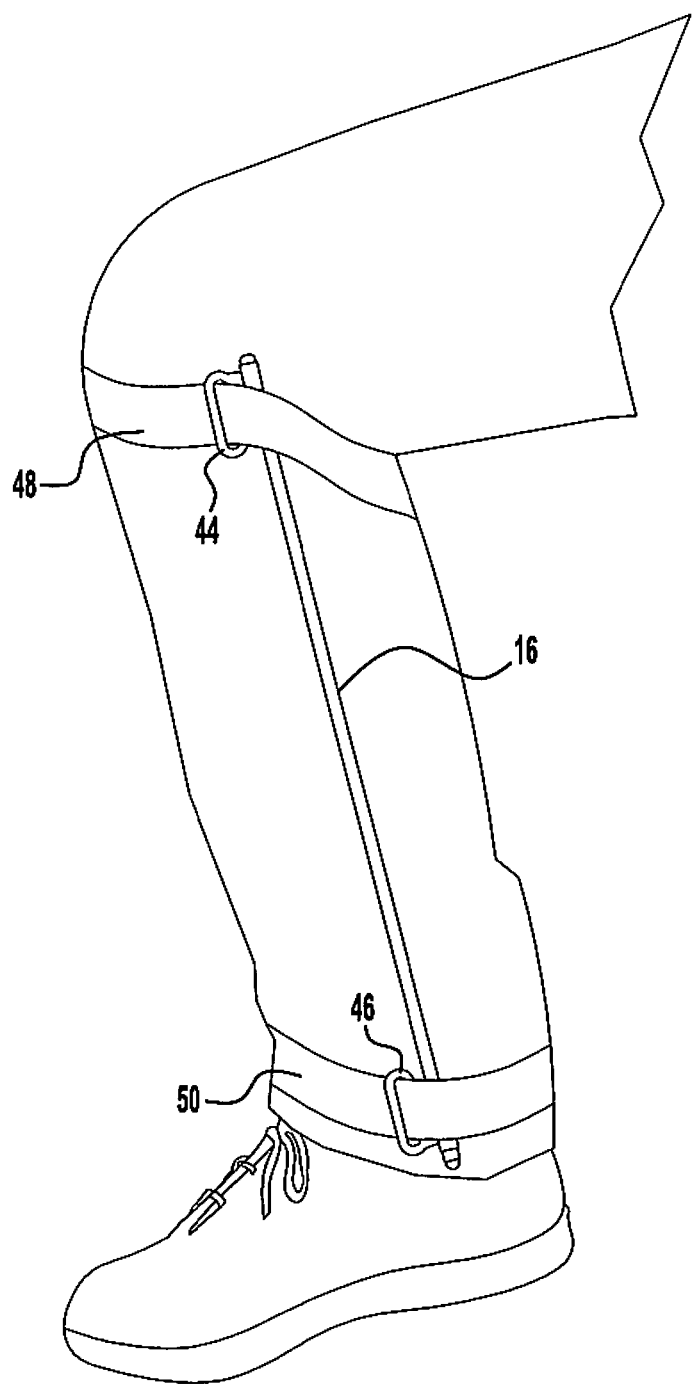
FIG. 6 shows the device for storing a laser optical fiber, as shown in FIG. 1, attached to the leg of a person, according to the present invention.

The storage housing 16 is removably attached to the leg of a patient (see FIG. 6), by any conventional means. For example, housing 16 can include one or two rings 44 and 46 through which straps 48 and 50, respectively, are inserted and used to attach the storage housing to the leg of patient. The straps 48 and 50 may be secured in a number of ways, including but not limited to Velcro enclosures, a flexible elastic, etc. While the housing 16 is illustrated as being attached to the leg of the patient, it is within the terms of the present invention to attach housing 16 to any other part of the patient's body or to a non-patient site in proximity to the surgical field.

The use of the present invention is typically during a medical procedure where a physician is using an optical fiber connected to a laser source 42 for emitting laser radiation. An advantage of the invention is the protection of the fragile laser optical fiber, which is expensive and prone to break if mishandled during medical procedures. Sometimes, the optical fiber is not needed and the proximal section 12 is placed somewhere where it can easily break or injure someone if the laser is accidentally fired. To alleviate this problem, the storage receptacle 16 is attached to a patient with straps 48 and 50 so that the physician can insert the proximal end 26 of optical fiber 14 into the receptacle 16 to keep it out of the way and to ensure that in the event of an accidental discharge of the laser light, the light won't cause damage to the staff, the patient or the equipment near the proximal end 26 of the optical fiber 14.

The medical grade stopper material is designed to be laser energy impermeable, as with the rest of housing 16. A length of laser fiber 14 can be pushed through the access port 24, preferably so that the walls of the access port 24 grip the optical fiber to keep the fiber in a stable position within the housing and to prevent any stray laser light from leaking out of the housing. Laser fiber 14 can extend through the cylindrically shaped section 16 as far as the end section 18 of housing 16. The interior of the hollow cylindrically shaped section 16 and the closed end section 18 are preferably coated with a material to absorb any stray laser light in the event a laser light is accidently fired through the laser optical fiber 14. This laser absorbing coating ensures that housing 16 is not laser energy permeable. The laser absorbing coating can be made of a material with specifications to ensure that an accidental discharge of the laser will be contained within the housing.

It is within the terms of the present invention to provide a housing 16 which can safely and effectively be used with any type or shape of laser fiber and/or laser source. That is, it is within the scope of the present invention to protect a laser delivery system that does not include an optic laser fiber during use or during a procedure, such a for example a ureteroscope (not shown). This embodiment of the invention used with a ureteroscope is substantially identical to the embodiment of a housing for a surgical fiber optic shown in FIGS. 1-6 and described above. The main difference is that the housing 16, as shown in FIG. 2, is designed to accommodate a length of fiber connected to a ureteroscope. Otherwise, the operation, design, and objective of housing 16 is substantially the same as the embodiments for accommodating a laser optical fiber as described herein before.

If desired, the length of the housing 16 can be adjustable. For example, cylindrically shaped section 16 can be constructed of telescoping portions (not shown), that allow the housing 16 to elongate or collapse, and to accommodate different lengths of optical fibers 14.

It is also within the terms of the present invention to connect two housings 16 adapted to house a laser fiber and the delivery system, such as for example a ureteroscope. The two housings can be constructed side by side as a contiguous unit. This embodiment, where the two housings are interconnected allows the two housings to work in conjunction with each other during a medical procedure. That is, for example, they can be together, attached to the leg of a patient in the manner shown in FIG. 6.

Figure 7:
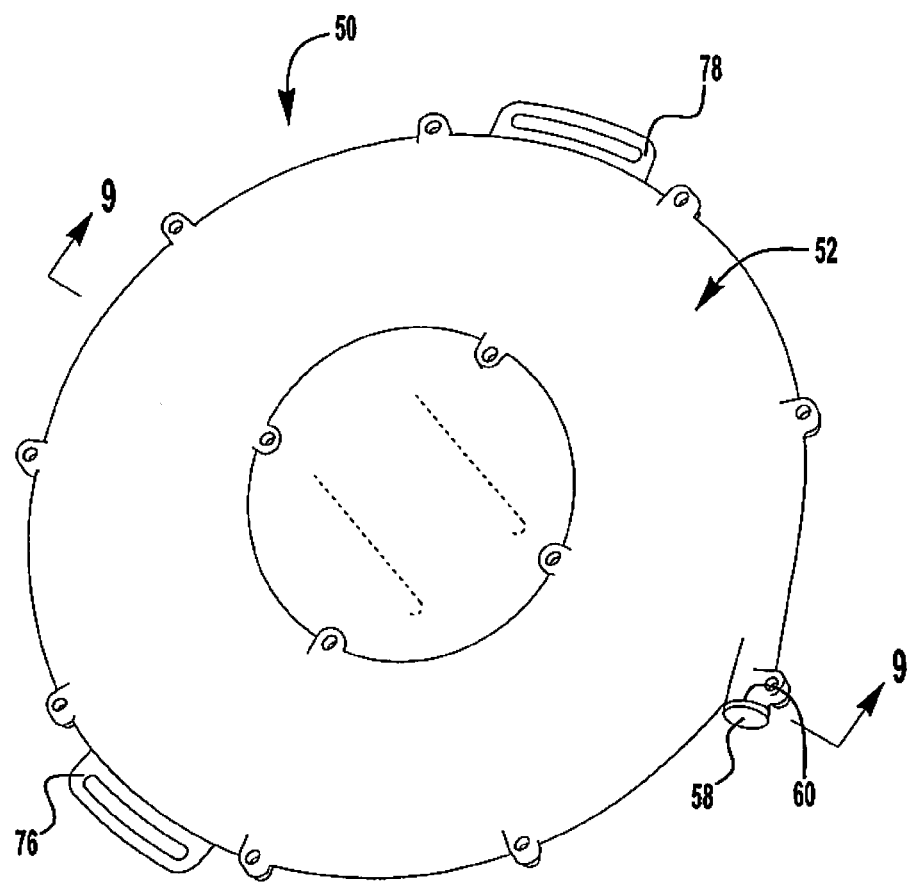
FIG. 7 shows a three dimensional view of another embodiment of a device for storing a laser optical fiber, according to the present invention.

Referring to FIG. 7, there is shown an alternative embodiment of the present invention a laser optical fiber storage system 50 that includes a storage receptacle or housing 52 for temporarily storing a proximal section or portion 54 of an elongated flexible optical fiber 56 (optical fiber 14). The storage housing 52 is configured to insert and retain the proximal section 54 of the optical fiber 56 in a coiled configuration and to enable the complete removal of the proximal portion therefrom.

A medical grade rubber plug or stopper 58 (see stopper 22) is disposed within the open end 60 of the elongated storage housing 52 to prevent the escape of laser light from within the storage housing. As with stopper 22, stopper 58 has an access port 62 adapted to enable the proximal portion section 54 of the optical fiber to be loaded into and withdrawn from the housing 52.

Figure 8:
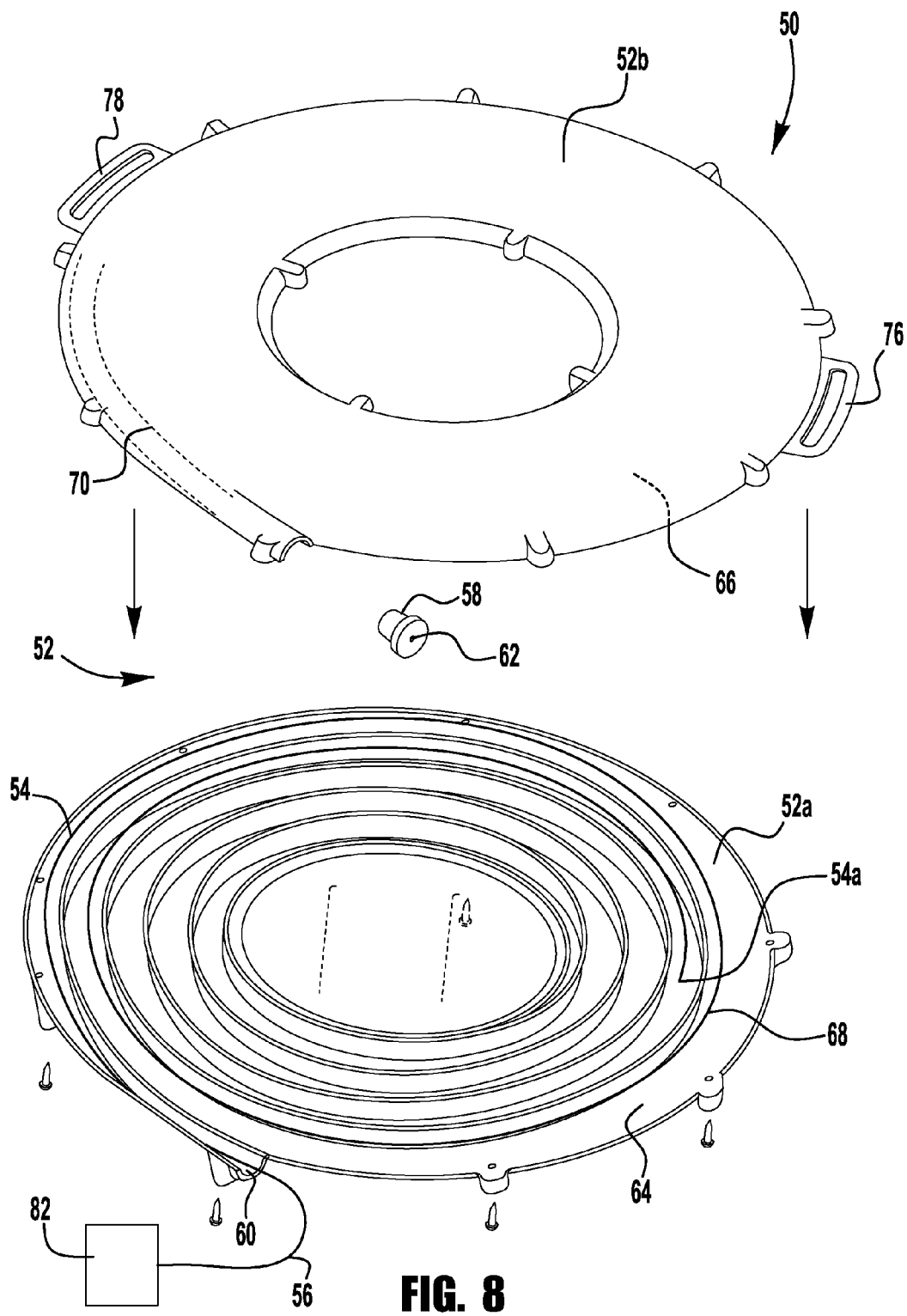
FIG. 8 shows an exploded view of the top and bottom portions of the device shown in FIG. 7 for storing a laser optical fiber, according to the present invention.

As shown in FIGS. 7, 8, and 9 a storage housing 52 is configured to temporarily retain the proximal section 54 of the elongated flexible optical fiber 54 in a coiled configuration.

As shown in FIG. 8, the inner walls 64 and 66 of storage housing sections 52a and 52b, respectively, are formed with spiral slots 68 and 70 on inner walls 64 and 66. When the two storage housing sections 52a and 52b are joined together, as shown in FIGS. 7 and 9, the spiral slots line up as shown in FIG. 9 to form a spiral shaped closed channel 71. The size of the channel 71 is adequate to receive an optical fiber 56. As discussed in more detail below, the proximal end 54a can be inserted into the housing 52 through the access port 62 of the rubber plug stopper 58. The spiral shaped channel 71 forms the elongated flexible optical fiber into a coiled configuration as shown in FIG. 8.

Generally, it is preferable that the proximal end 54 of the optical fiber 56 does not contact the inner wall 28 of the receptacle 16. However, it is within the terms of the invention that the proximal end 26 can contact the inner wall of the receptacle when the inner wall is constructed of a variety of materials as discussed hereinafter.

The storage housing 52 is preferably constructed as a clam shaped housing with an open end 60. The housing 52 can be formed of the two circular storage housing sections 52a and 52b which are the mirror image of each other. When they are joined together as indicated in FIG. 9, they form the spiral shaped channel 71. While screws are indicated as the means to join the housing sections 52a and 52b together, it is within the terms of the invention to join them in any desirable way, such as with an adhesive. The housing 52 can be constructed of a variety of materials, such as but not limited to, for example, plastic, polymers and aluminum. The open end 60 receives a closure element, such as for example, a medical grade rubber stopper 58 having an access port 62 extending there through. The material of the medical grade stopper 58 is designed to be laser energy impermeable, as with the rest of housing 52.

Similar to the embodiment shown in FIG. 2, hollow housing 52 can have a structure for preventing laser light from passing through walls of the storage housing. The structure can be comprised of an inner liner 72, see FIG. 9, having a spiral shape to be received in the channel 71. As with the inner liner 30 shown in FIG. 2, the liner 72 can be of a material such as silicone rubber (no latex) which blocks laser beams of all wavelengths. The silicone rubber can be loaded with a substantial amount of particulate material to resist penetration of the structure by a medical laser beam for at least a desirable time interval.

Another material suitable for the inner liner and that is substantially non-burnable when exposed to a medical laser beam so as to resist penetration of the structure by a medical laser beam for at least a desirable time interval is a silicone rubber (no latex) which blocks laser beams of all wavelengths from Lasermet Ltd. of Georgia.

The inner liner 72 can be a coating on the inner wall 74 of the channel 71 of housing 52. Alternatively, the inner liner 30 can be constructed as a tube which is sized to firmly fit within the channel 71 of housing 52. This type of silicone rubber is substantially non-burnable when exposed to a medical laser beam and is able to resist burn-through by the medical laser beam of the inner liner and the housing wall when exposed to a medical laser beam for at least a desirable time interval.

It is also within the terms to fill the channel 71 with a gel 73, as shown in FIG. 10, such as for example, an acoustic gel with the trade name LithoClear from Sonotech Corporation of Washington, in the same manner a illustrated in FIG. 3. The gel 73, which is approximately 90% water, provides very good protection to the housing 52 and is able to resist burn-through of the housing wall when exposed to a medical laser beam for a period of time. The gel 73 will be contained within the housing 52 by the plug stopper 58. Note that the gel 73 is very viscous and as such can easily be contained within the channel 71 of housing 52 by the stopper 58.

Another embodiment of the present invention, as shown in FIG. 11, is the incorporation of the inner liner 72 in combination with the gel 73, described directly above.

Referring again to plug stopper 58, it can be constructed the same as plug stopper 22, described herein before. The access port 62 through which an optical fiber 56 can be inserted into the housing 52 extends through the head portion of plug stopper 58. Note that the access port 62 is generally contracted into a closed condition. However, port 62 can expand to allow the optical fiber 56 to be pushed though and into the housing 52. Once the optical fiber 56 passes through the access port 62, it contracts and holds the optical fiber in place so that it won't slip out of the housing 52. The closed access port 62 also keeps the gel 73 within housing 52 when it is incorporated into the design. Moreover, when the optical fiber 56 is removed from the gel filled housing 52, the gripping of the fiber by the contracted access port 62 causes the gel to be wiped off of the fiber as it is being withdrawn. Another advantage of the closed access port 62 is that when an optical fiber 56 is inserted through the access port and into the housing 52, the closure of the access port grips the optical fiber and prevents any stray laser light from escaping the housing 52 in the case that the laser is accidentally fired off.

Figure 12:
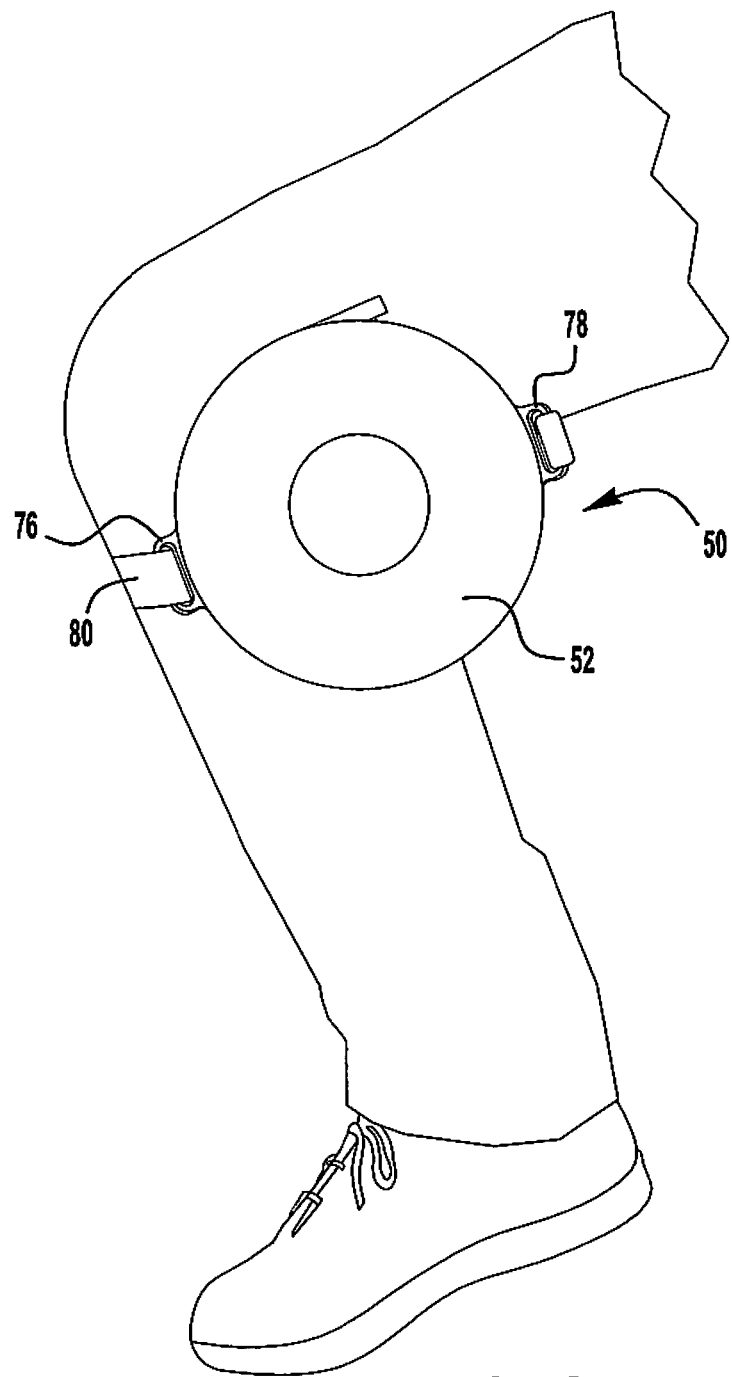
FIG. 12 shows the device for storing a laser optical fiber, as shown in FIG. 7 attached to the leg of a person, according to the present invention.

The storage housing 52 can be removably attached to the leg of a patient (see FIG. 12), by any conventional means. For example, housing 52 can include one or two rings 76 and 78 through which a strap 80 is inserted and used to attach the storage housing to the leg of patient. The strap 80 may be secured in a number of ways, including but not limited to Velcro enclosures, a flexible elastic, etc. While the housing 52 is illustrated as being attached to the leg of the patient, it is within the terms of the present invention to attach housing 52 to any other part of the patient's body or to a non-patient site in proximity to the surgical field.

As with the other embodiments described herein, the present invention is typically used during a medical procedure where a physician is using an optical fiber connected to a laser source 82, as shown in FIG. 8, for emitting laser radiation. One advantage of the invention is to protect the fragile laser optical fiber 56, which is expensive and prone to break if mishandled, during medical procedures. Sometimes, during the optical fiber 56 is temporarily not needed and the proximal section 54 is placed somewhere where it can easily break or injure someone if the laser is accidentally fired. To alleviate this problem, the storage receptacle 52 can be attached to a patient with a strap 80 so that the physician can insert the proximal end 54a of optical fiber 56 into the housing 52 to keep it out of the way and to ensure that in the event of an accidental discharge of the laser light, the light won't cause damage to the staff, the patient or the equipment near the proximal end 54a of the optical fiber 56.

In operation, the proximal end 54a of a length of laser fiber 56 can be pushed through access port 62 adapted to enable the proximal portion of the laser fiber to be withdrawn from and reloaded into the housing. The walls of access port 62 grip the fiber 56 to keep the fiber in a stable position within the housing 52 and to prevent any stray laser light from leaking out of the housing. Laser fiber 56 can follow the spiral channel 71 and form a coil, as generally shown in FIG. 8. Upon removal from the housing 52, the proximal portion 54 of the laser fiber 56 will return substantially to its elongate, uncoiled configuration.

Being that the channel 71 is filled with a gel 73 as shown in FIG. 10 or preferably coated with a material 72 to absorb any stray laser light or incorporates an inner liner 72 and is filled with a gel as shown in FIG. 11, as previously described with regards to FIGS. 3 and 4, each made of a material with specifications to ensure that an accidental discharge of the laser will be contained within the housing, in the event a laser light is accidentally fired through the laser optical fiber 56.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

What is claimed is:

1. A laser optical fiber storage system characterized by:
a storage housing having only one open end through which a proximal end of an elongated optical fiber can be pushed into, withdrawn from, and reloaded into the storage housing while the elongated optical fiber remains connected to a laser source for emitting laser light; and
structure within the storage housing for preventing laser light from escaping from the open end of the storage housing in the event of a discharge of the laser light from the optical fiber while the proximal end section of the elongated optical fiber is retained within the storage housing.

2. The laser optical fiber storage system of claim 1 characterized in that the structure within the storage housing for preventing laser light from escaping from the storage housing is a liner of silicone rubber which prevents laser beams from passing therethrough.

3. The laser optical fiber storage system of claim 2 characterized in that the liner of silicone rubber is a flexible matrix which is non-burnable when exposed to medical laser beams.

4. The laser optical fiber storage system of claim 3 characterized in that the liner is a coating on the inner wall of the storage housing.

5. The laser optical fiber storage system of claim 2 characterized in that the liner is a tube which is sized to fit within the storage housing.

6. The laser optical fiber storage system of claim 1 characterized in that the structure within the storage housing for preventing laser light from escaping from the storage housing is a gel for preventing laser light from passing through walls of the storage housing.

7. The laser optical fiber storage system of claim 1 characterized in that the structure within the storage housing for preventing laser light from escaping from the storage housing is an inner liner of silicone rubber which blocks laser beams and a gel within the inner liner for preventing laser light from passing through walls of the storage housing.

8. The laser optical fiber storage system of claim 1 characterized in that a plug stopper being laser energy impermeable is disposed within the open end of the storage housing to prevent the escape of laser light from within the storage housing; and
an access port through the plug stopper is generally contracted into a closed condition and can expand for the optical fiber to be pushed through and into the housing and to contract to hold the optical fiber within the housing.

9. The laser optical fiber storage system of claim 2 characterized in that the housing includes at least one ring through which a strap is inserted for attaching the storage housing to a patient's body.

10. A laser optical fiber storage system, characterized by:
a closed storage housing having only one open end for inserting the proximal section of an optical fiber connected to a laser source for emitting laser radiation and for retaining the optical fiber in a coiled configuration and to enable the complete removal of the proximal portion there from; and
structure within the storage housing for preventing laser light from escaping from the storage housing in the event of a discharge of the laser light when the proximal end section is retained within the storage housing.

11. The laser optical fiber storage system of claim 10 characterized in that the closed storage housing has a spiral shaped closed channel connected to the open end to receive the proximal section of the optical fiber and to configure the optical fiber in a coiled configuration.

12. The laser optical fiber storage system of claim 11 characterized in that the structure within the storage housing for preventing laser light from escaping from the closed storage housing is an inner liner of silicone rubber within the spiral shaped closed channel which prevents laser beams from passing therethough.

13. The laser optical fiber storage system of claim 12 characterized in that the inner liner is a coating of silicone rubber that is substantially non-burnable when exposed to a medical laser beam so as to resist penetration through the structure by a medical laser beam for at least a desirable time interval.

14. The laser optical fiber storage system of claim 12 characterized in that the inner liner is configured as a tube which is sized to fit within the spiral shaped closed channel of the storage housing.

15. The laser optical fiber storage system of claim 11 characterized in that the structure within the storage housing for preventing laser light from passing through walls of the storage housing is a gel which is within the spiral shaped closed channel of the storage housing.

16. The laser optical fiber storage system of claim 11 characterized in that the structure within the storage housing for preventing laser light from escaping from the storage housing is an inner liner of silicone rubber which blocks laser beams and a gel within the inner liner for preventing laser light from passing through walls of the storage receptacle.

17. The laser optical fiber storage system of claim 11 characterized in that a plug stopper having an access port is disposed within the open end of the storage housing to prevent the escape of laser light therefrom; and
the access port through the plug stopper is generally contracted into a closed condition and can expand for the optical fiber being pushed through and into the housing and contract to hold the optical fiber within the storage housing.

18. A method of temporarily storing an elongated flexible optical fiber, comprising:
providing a closed elongated storage housing having only one open end through which a proximal end of the optical fiber can be pushed into, withdrawn from and reloaded into the housing while the elongated optical fiber remains connected to a laser source for emitting laser light;
inserting a proximal end section of the optical fiber into the open end of the closed storage housing;
temporarily retaining the proximal end section of the elongated flexible optical fiber within the closed storage housing;
preventing the laser light from escaping the closed storage housing in the event of a discharge of the laser light when the proximal end section is retained within the closed storage housing; and
removing the proximal end section of the optical fiber from the open end of the closed storage housing.

19. The method of claim 18 including the step of temporarily retaining the proximal section of the elongated flexible optical fiber while in an elongated configuration.

20. The method of claim 18 including the step of retaining the proximal section of the elongated flexible optical fiber in a spiral configuration.

\* \* \* \* \*